US012594434B2

(12) United States Patent
Van Abeelen et al.

(10) Patent No.: US 12,594,434 B2
(45) Date of Patent: Apr. 7, 2026

(54) OPTICAL ASSEMBLY FOR USE IN A SKIN TREATMENT DEVICE

(71) Applicant: KONINKLIJKE PHILIPS N.V., Eindhoven (NL)

(72) Inventors: Frank Anton Van Abeelen, Eindhoven (NL); Rieko Verhagen, Vught (NL); Boamfa Marius Iosif, Veldhoven (NL); Kiran Kumar Thumma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 356 days.

(21) Appl. No.: 18/570,159

(22) PCT Filed: Jun. 9, 2022

(86) PCT No.: PCT/EP2022/065651
§ 371 (c)(1),
(2) Date: Dec. 14, 2023

(87) PCT Pub. No.: WO2022/263274
PCT Pub. Date: Dec. 22, 2022

(65) Prior Publication Data
US 2025/0128088 A1 Apr. 24, 2025

(30) Foreign Application Priority Data
Jun. 18, 2021 (EP) ..................................... 21180439

(51) Int. Cl.
A61N 5/06 (2006.01)
A61B 5/00 (2006.01)
(Continued)

(52) U.S. Cl.
CPC ............ A61N 5/0616 (2013.01); A61B 5/444 (2013.01); G02B 6/0025 (2013.01);
(Continued)

(58) Field of Classification Search
None
See application file for complete search history.

(56) References Cited

U.S. PATENT DOCUMENTS 7,097,656 B1 8/2006 Akopov et al.
7,153,015 B2 12/2006 Brukilacchio
(Continued)

FOREIGN PATENT DOCUMENTS

EP 3281598 A1 2/2018
EP 3610818 A1 2/2020
KR 100938378 B1 1/2010

OTHER PUBLICATIONS

International Search report and Written Opinion of PCT/EP2022/065651, dated Aug. 31, 2022.

*Primary Examiner* — Richard H Kim

(57) ABSTRACT

Provided is an optical assembly (1) for use in a skin treatment device (2), and the use thereof in a treatment method. The optical assembly (1) comprises a light source (10), a first prism (11) and first and second guiding elements (12) and (13) with enclosed reflective faces disposed facing each other. The first prism (11) includes a first surface (111), a second surface (112) inclined with the first surface (111) and a third surface (113) adjoining the first (111) and the second (112) surfaces. The first guiding element (12) is arranged to guide the light transmitted from the light source (10) through the first surface (111) of the first prism. The second guiding element is further arranged to receive through the second surface (112) of the first prism (11), the light reflected from the third surface (113) of the first prism and output the received light for illuminating the skin. The first surface (111) and the second surface (112) of the first prism (11) are separated from the first guiding element (12)
(Continued)

and the second guiding element (13), respectively, by a refractive index interface and act as total internal reflection surfaces.

15 Claims, 11 Drawing Sheets

(51) Int. Cl.
    *A61B 18/00*     (2006.01)
    *A61B 18/18*     (2006.01)
    *F21V 8/00*     (2006.01)

(52) U.S. Cl.
    CPC .. *G02B 6/0053* (2013.01); *A61B 2018/00476* (2013.01); *A61B 2018/1807* (2013.01); *A61N 5/0617* (2013.01); *A61N 2005/063* (2013.01); *A61N 2005/0666* (2013.01)

(56)              References Cited

U.S. PATENT DOCUMENTS

| | | | |
|---|---|---|---|
| 9,295,518 | B2 | 3/2016 | Verhagen et al. |
| 2011/0190749 | A1 | 8/2011 | Mcmillan et al. |
| 2016/0074672 | A1 | 3/2016 | Schomacker et al. |
| 2017/0246473 | A1 | 8/2017 | Marinkovich et al. |

Figure 3c
Figure 3b
Figure 3d
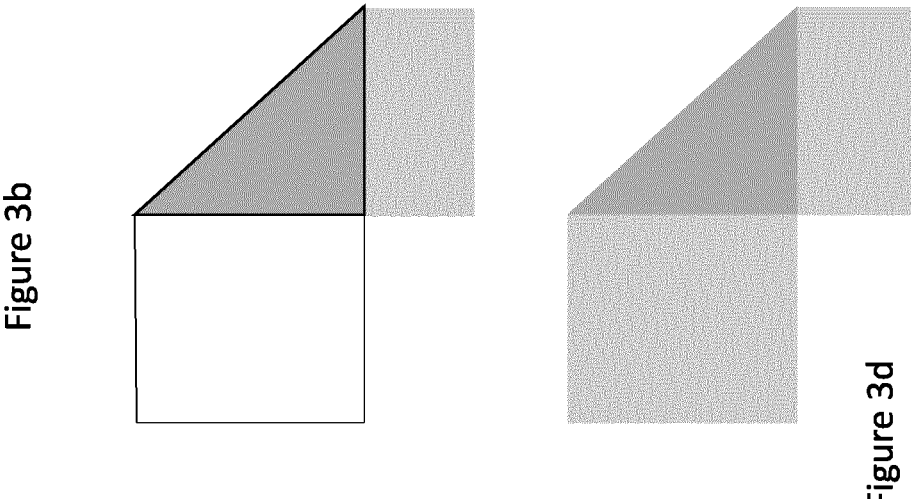
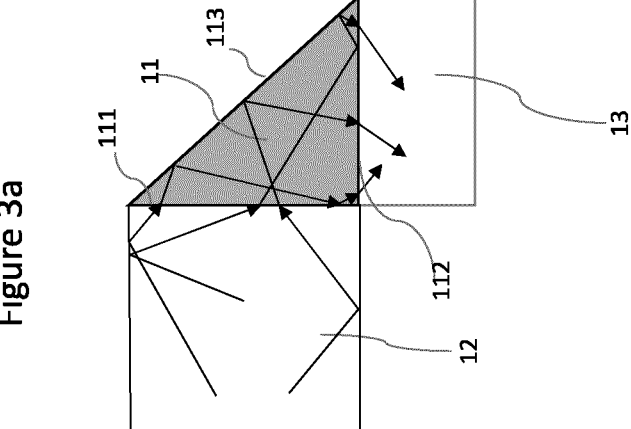
Figure 3a

OPTICAL ASSEMBLY FOR USE IN A SKIN TREATMENT DEVICE

CROSS-REFERENCE TO PRIOR APPLICATIONS

This application is the U.S. National Phase application under 35 U.S.C. § 371 of International Application No. PCT/EP2022/065651, filed on Jun. 9, 2022, which claims the benefit of European Patent Application No. 21180439.8, filed on Jun. 18, 2021. These applications are hereby incorporated by reference herein.

FIELD OF THE INVENTION

The invention relates to an optical assembly for use in a skin treatment device, preferably, a photoepilation device, more preferably, an intense pulsed light-based device. The invention further relates to the device comprising the optical assembly, and a method of using the assembly in the device.

BACKGROUND OF THE INVENTION

Pulsed light can be used for performing hair or skin treatment such as cosmetic hair removal. The light pulse is generated using sources such as lamps, light bulbs, light emitting diodes or lasers. It penetrates the skin and is absorbed, e.g. in the root of the hair. The temperature of the root of the hair consequently rises. The growth of the hair is inhibited if the temperature rise is sufficiently high. This process is known as selective photothermolysis.

Light-based treatment devices, such as intense pulsed light (IPL) devices, photo epilation devices, skin rejuvenation devices, phototherapy devices or pain relief devices, often use incoherent light for skin or hair treatment. For example, IPL technology uses light from e.g. a halogen, e.g. Xe, flash lamp at a relatively low fluence (up to 6.5 J/cm2) (as compared to professional devices, for permanent photoepilation, that use fluences in excess of 10 J/cm2), and relatively high beam divergence (e.g. compared to lasers).

EP 3 281 598 A1 discloses a laser skin treatment device for laser induced optical breakdown of hair or skin tissue. A beam scanning system scans the beam using a rotated prism which implements a lateral shift to the beam. A focusing system at the output side of the beam scanning system focuses the incident light beam into a focal spot in the tissue.

SUMMARY OF THE INVENTION

In contrast to treatment devices where optical fibers are used as waveguides to guide light to a target (skin), in devices using prism-based light waveguides, the treatment light needs to be bent at relatively large angles (e.g. 90 degrees) to be guided effectively to the skin. The inventors of the present invention have recognized that it is not always possible to achieve such guidance in the latter. For example, as shown in FIG. 1, light rays may bypass reflection at the prism, so that they are incident at incorrect angles in the waveguide. Moreover, since some rays are reflected and others not, there is a non-uniform angular and spatial distribution of the light beam/treatment light in the device. Such rays are not effectively directed to the target. Furthermore, due to the incoherent light source characteristics of the device, the emitted light is diffuse and characterized by a wide range of propagation angles. It is an object of the invention to provide an optical assembly to effectively guide such diffuse light using a prism-based optical waveguide, ensure uniformity of the treatment light, and in turn improve device treatment efficiency. It is a further object of the invention to reduce light leakage while guiding the light through the waveguide.

Another problem, as shown in FIG. 1, is that while using prism-based waveguides, even after undergoing reflection in the prism, some incident light/rays may be redirected towards the treatment source. This may happen when light rays are incident on a sub-optimal position on the reflective surface of the prism, e.g. on an upper part of the prism hypotenuse. It is another object of the invention to provide an optical assembly which increases the flux of incident light directed towards the target by reducing such back propagation of light.

Additionally, prior to treatment, it is desirable to obtain characteristics (e.g. pigmentation) of the skin/target positioned adjacent to a device treatment aperture via which the treatment light pulses are applied to the skin. Other aspects like detection of skin contact, hair count or displacement and motion of the device are equally desirable. For example, if no skin contact or an unsafe skin tone is detected, the device is prevented from flashing. It is yet another object of the invention to provide an optical assembly which facilitates incorporation of further optical elements which can carry out these functions. According to an aspect, an optical assembly for use in a skin treatment device is provided. The optical assembly comprises a light source, a first prism and first and second guiding elements with bound/enclosed reflective faces disposed opposite to or facing each other. The first prism includes a first surface, a second surface inclined with the first surface and a third surface adjoining the first and the second surfaces. The first guiding element is arranged to guide the light transmitted from the light source through the first surface of the first prism to its third surface. The second guiding element is further arranged to receive through the second surface of the first prism, the light reflected from the third surface of the first prism and output the received light for illuminating a target/body part (skin). The first surface and the second surface of the first prism are separated from the first guiding element and the second guiding element, respectively, by a refractive index interface. In other words, there exists a material which is different from the prism material, in contact with each of the first surface and the second surface. The first and second surfaces are total internal reflection surfaces. According to another aspect, a method is provided for performing a cosmetic or non-therapeutic treatment of the target using the optical assembly.

According to an aspect, the third surface of the first prism or a surface of the second guiding element is coated, at least partially, with a reflective coating e.g. on an outer side. According to an aspect, the first prism and/or the first light guiding element and/or the second light guiding element is a total internal reflection (TIR) guiding element. When the first prism acts as a TIR element, the first and/or second surfaces of the first prism are disposed in contact with a medium (e.g. the material of the adjacent guiding element) of a refractive index less than a refractive index $n_p$ of the first prism.

The third surface of the first prism may further be in contact with a medium of lower refractive index (air or a reflective coating). When the first or the second guiding element acts as a TIR element, the reflective faces of the first light guiding element and/or the reflective faces of the second guiding element are disposed in contact with air (medium of lower refractive index).

According to an aspect, a light exit face of the first guiding element and/or a light entry face of the second guiding element are separated by a predetermined gap from the first surface of the first prism and the second surface of the first prism, respectively. The gap further comprises a dielectric material, wherein the dielectric material has a lower refractive index than a refractive index of the first prism. The gap may further comprise metallic, glass and/or ceramic particles.

According to an aspect, the optical assembly further comprises a second prism having a first surface and second surface inclined with each other and a third surface adjoining the first and the second surfaces, wherein the third surface of the second prism is removably attached or fused to a portion of the third surface of the first prism or a reflective surface of the second guiding element, and such that the first surface of the second prism is disposed substantially parallel to the second surface of the first prism. The second surface of the second prism may comprise a reflective coating, e.g. on its outer side. The third surface of the second prism may further include a deformable layer such as a transparent silicone layer. The second surface of the second prism may be connected to a movable actuator.

According to an aspect, the optical assembly further comprises an imaging element for imaging the target through the first surface of the second prism. The imaging element may be mounted on the first surface or another suitable component of the optical assembly for this purpose.

According to an aspect, there is provided a light filter and/or an insulating window in the optical assembly. A cooling member is further provided in thermal contact with the first prism.

According to an aspect, a device comprising the above-mentioned optical assembly is provided, which is suitable for treating a body part/skin of a user. According to an aspect, the second guiding element is disposed in a removable attachment of the device.

According to an aspect, a computer-implemented method for performing cosmetic or non-therapeutic treatment of skin is provided. The method comprises providing an optical assembly as mentioned, determining, based on at least one image obtained by an imaging element of the optical assembly whether or not to perform the treatment, and if yes, guiding light emitted by a light source of the optical assembly to the target for performing the treatment.

These and other aspects, and further advantages, will be apparent from and elucidated with reference to the embodiment(s) described herein.

BRIEF DESCRIPTION OF THE DRAWINGS

FIGS. 3a-d show optical assembly 1 according to a second exemplary embodiment of the invention.

DETAILED DESCRIPTION OF THE EMBODIMENTS

Figure 1:
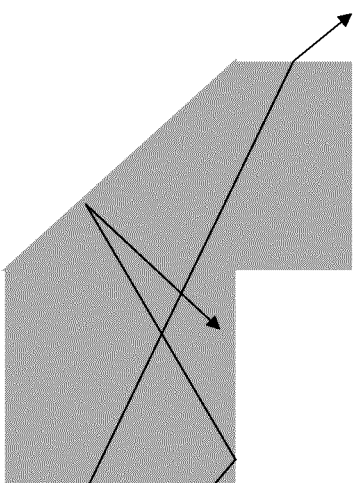
FIG. 1 shows a prism-based waveguide without a refractive index variation therein.

The matters exemplified in this description are provided to assist in a comprehensive understanding of various exemplary embodiments of the present invention disclosed with reference to the accompanying figures.

Accordingly, those of ordinary skill in the art will recognize that various changes and modifications of the exemplary embodiments described herein can be made without departing from the scope of the claimed invention. In particular, combinations of specific features of various aspects of the invention may be made. An aspect or embodiment of the invention may be further advantageously enhanced by adding a feature that was described in relation to another aspect or embodiment of the invention.

Further, the functionality associated with any particular means may be centralized or distributed, whether locally or remotely. A computer program may be stored/distributed on a suitable medium, such as an optical storage medium or a solid-state medium supplied together with or as part of other hardware, but may also be distributed in other forms, such as via the Internet or other wired or wireless telecommunication systems. It may be advantageous to set forth that the terms "include" and "comprise," as well as derivatives thereof, mean inclusion without limitation. In addition, reference to an element by the indefinite article "a" or "an" does not exclude the possibility that more than one of the element is present, unless the context clearly requires that there be one and only one of the elements. The indefinite article "a" or "an" thus usually means "at least one".

The expression "at least one of A, B and C" means "A, B, and/or C", and that it suffices if e.g. only B is present. Any reference signs in the claims should not be construed as limiting the scope.

A surface is defined herein to refer to the faces of various optical components. The skilled person imparts the same meaning to these terminologies.

The light emitted by a light source (one or more) for treatment purposes is referred to as "treatment light". The light-based treatment device may comprise further light sources for emitting light that is not used as treatment light.

Although the method may be intended towards cosmetic treatment, the use of the device for medical treatments is not excluded herein. Further, although the method may be performed at home, it goes without saying that the method may also be practically exploited in an industrial setting, for example, in commercial salons.

The term "user" used herein may be used to refer also to the person using the device, and not necessarily the target whose skin is treated.

The term "guiding element" encompasses any element having sufficient dimensions (length, width or height equal to or different from one another) which can guide light. These elements may be elongated, and have shapes such as rectangular, square, triangular (e.g. a prism), trapezoid, planar, curved or a hybrid of planar and curved (e.g. plano-concave) and the like. Guiding elements 12 and 13 may further comprise fully or partially bound surfaces (faces).

Figures 2A, 2B:
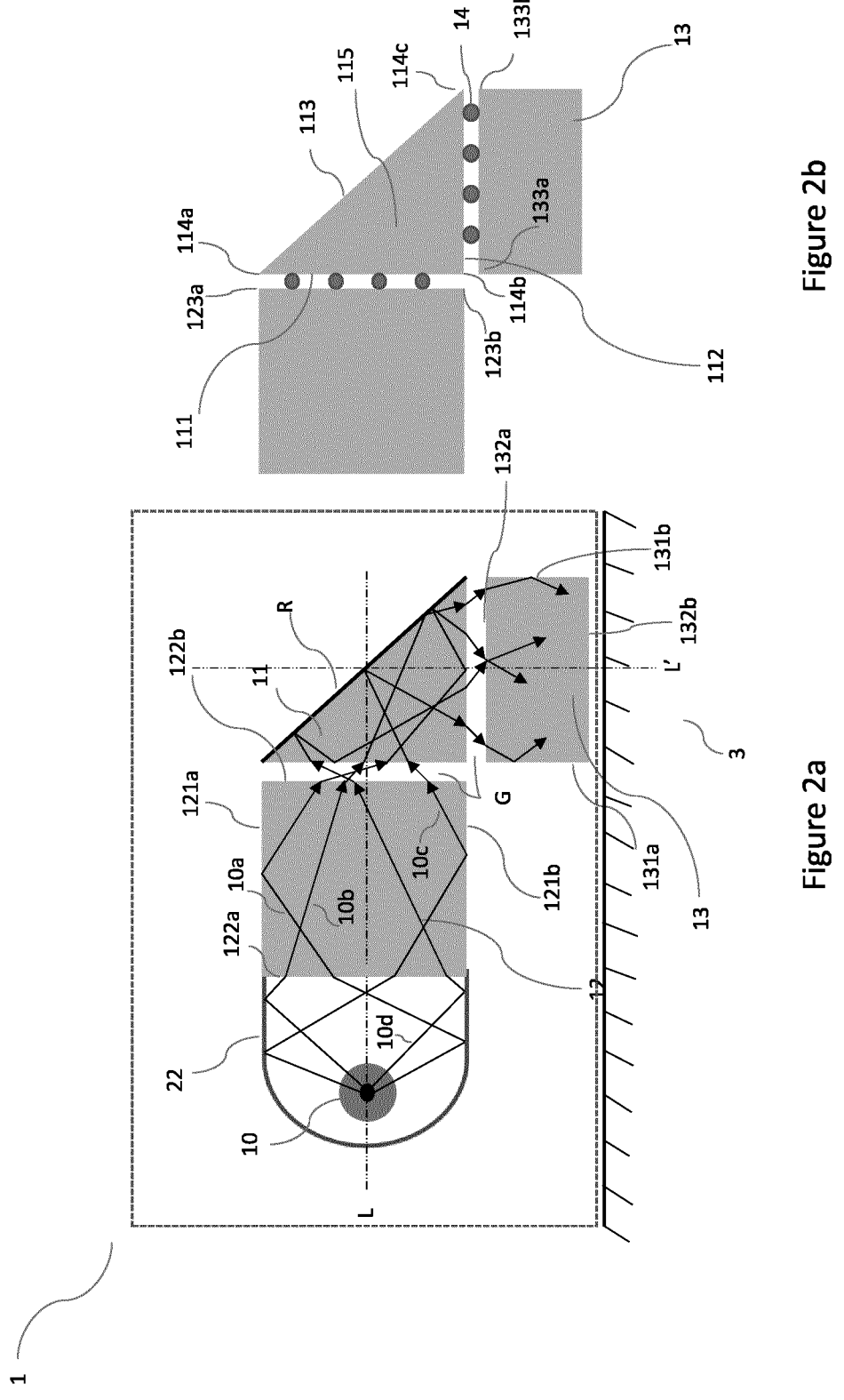
FIGS. 2a and 2b show optical assembly 1 according to an exemplary embodiment of the invention.

FIGS. 2a and 2b show top cross-sectional views of optical arrangement 1 according to an exemplary embodiment of the invention. The arrangement can be positioned inside a skin or hair treatment device, such as the IPL device.

The optical arrangement 1 comprises light source 10 which can generate light for illuminating and thus treating target 3. The light source 10 can generate light pulses of any suitable or desired wavelength (or range of wavelengths) and/or intensities. For example, the light source 10 can generate visible light, infra-red (IR) light and/or ultraviolet (UV) light. In an embodiment, the arrangement comprises multiple light sources 10. Each light source 10 can comprise any suitable type of light source, such as one or more light emitting diodes (LEDs), a (Xenon) flash lamp, one or more lasers (e.g. laser diodes, VCSELs), etc. The light source(s) 10 can provide light pulses with spectral content in the 530-1200 nanometre (nm) range for a duration of around 2.5 milliseconds (ms), as these wavelengths heat melanin in the hair and hair root by absorption, which puts the hair follicles in a resting phase, preventing hair regrowth. These wavelengths further enable a contrast in absorption between the hair and surrounding dermis and ensure that light is minimally absorbed by the latter. In an embodiment, light source 10 is a broadband light source which emits light in a broad spectrum of wavelengths or frequencies.

The optical arrangement further comprises a prism (first prism 11) which is arranged to receive the light emitted from the light source 10. First prism 11 comprises a first surface 111, a second surface 112 inclined with the first surface 111 and a third surface 113 adjoining the first 111 and the second 112 surfaces. The geometry of a prism, e.g. that the prism includes more surfaces than those exemplified in the drawings, is well-known to those skilled in the art. In an embodiment, the first surface 111 and the second surface 112 may be two orthogonal surfaces of a right-angled prism, preferably, a right-angled isosceles prism, and the third surface 113, the oblique surface (hypotenuse) which connects the orthogonal first surface 111 and the second surface 112. This prism configuration results in a light path which is bent by 90 degrees, i.e. the angle between the first surface 111 and the second surface 112. Other prism configurations result in light bending angles corresponding to the angle between their respective first surface 111 and the second surface 112. First prism 11 may be made of material with a suitable refractive index $n_p$.

Guiding elements 12 and 13 are further illustrated in FIGS. 2a and 2b as part of the optical assembly 1.

For example, guiding element 12 may comprise surfaces 121a, 121b, 122a and 122b, where surfaces 121a and 121b face each other on opposite sides of the first guiding element 12, e.g. on opposite sides of an axis L through the light source 10, the first guiding element 12 and the first prism 11. Surfaces 122a and 122b face each other on another two opposite sides of the guiding element 12 and extend perpendicular to said axis. Surfaces 121a and 121b are further bound (closed) surfaces. Hence, surfaces 122a and 122b enclose the guiding element 12 from opposite directions. Surfaces 121a, 121b, 122a and 122b may be regarded as top, bottom and two side surfaces of the first guiding element 12 herein.

The first guiding element 12 is disposed between the light source and the first prism 11 such that the light emitted from the light source 10 is guided therethrough to the first surface 111 of the first prism 11. Air may be present as medium between light source 10 and the first guiding element 12, so that the light emitted from the light source 10 travels through air (refractive index n=1) to the first guiding element 12. Opposite facing side surfaces/faces 122a and 122b act as light entry and light exit faces, respectively, for light emitted from the light source 10. Edge 123a separating top surface 121a and side surface 122b of the first guiding element 12 may be positioned to be flush with edge 114a separating first surface 111 and third surface 113 of the first prism 11. Edge 123b separating bottom surface 121b and side surface 122b of the first guiding element 12 may be positioned to be flush with edge 114b separating first surface 111 and second surface 112 of the first prism 11.

Similarly, bound surfaces 131a and 131b face each other on opposite sides of the second guiding element 13 e.g. on opposite sides of an axis L' through the second guiding element 13 and the first prism 11. Hence, surfaces 131a and 131b enclose the guiding element 13 from opposite directions. The second guiding element 13 is arranged to receive, through the second surface 112 of the first prism 11, the light reflected from the third surface 113 of the first prism and output it for illuminating and thereby treating the target 3 (body part e.g. skin or hair, of a user). Light incident on bound surfaces 131a and 131b is reflected by these surfaces towards the treatment aperture. Depending on the dimensions of the first guiding element 12 and the second guiding element 13, multiple reflections may occur at 121a, 121b and 131a, 131b. Such reflections are not excluded herein.

Figure 7:
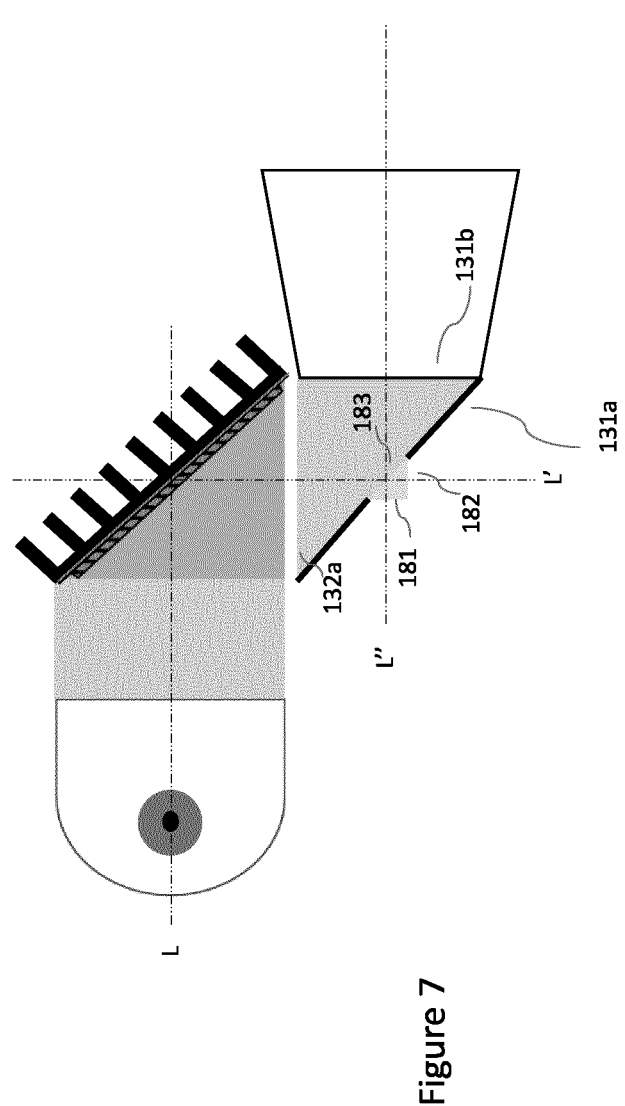
FIG. 7 shows optical assembly 1 according to a sixth exemplary embodiment of the invention.

In the embodiment of FIG. 2a/2b, opposite facing surfaces 132a and 132b which extend perpendicular to axis L' act as light entry and light exit faces, respectively, for light reflected from the third surface 113 of the first prism 11. Surfaces 131a, 131b, 132a and 132b may be regarded as side, top and bottom surfaces of the second guiding element 13 herein. In an embodiment, e.g. as shown in FIG. 7, surfaces 131a and 131b may simply face each other at an inclination, i.e. without being parallel to each other. In this case, surface 131a may bisect axis L' and be adjoined to surface 131b which is parallel to axis L'. Surface 132a may connect surfaces 131a and 131b, so that the second guiding element 13 takes the shape of a prism. Hence, it is not essential for guiding element 13 to comprise surface 132b. Here, surface 131b acts as the light exit face, as shown in FIG. 7.

Edge 133a separating side surface 131a and top surface 132a of the second guiding element 13 may be positioned to be flush with edge 114b separating first surface 111 and second surface 112 of the first prism 11. Edge 133b separating side surface 131b and top surface 132a of the second guiding element 13 may be positioned to be flush with edge 114c separating second surface 112 and third surface 113 of the first prism 11.

As a result of bound top and bottom surfaces 121a and 121b of guiding element 12 and side surfaces 131a and 131b of guiding element 13, both the treatment light emitted from light source 10, and that reflected from the third surface 113 of the first prism 11 are confined to the interior of the respective guiding element, reducing losses due to beam divergence. This in turn increases the amount of light flux incident on the target 3. The bound surfaces of guiding elements 12 and 13 are further reflective (e.g. made of metal, glass), so that any diverging treatment light is reflected by the bound surfaces and (re)-guided towards the first surface 111 of the first prism 11 or towards the treatment aperture to target 3, further increasing the amount of light flux incident on the target 3.

The multi-element (therefore including multiple refractive interfaces) optical assembly comprising the first prism 11 (e.g. a solid prism), the first guiding element 12 and the second guiding element 13 creates refractive index variations/differences at surfaces 111 and 112 of the first prism 11. Light rays 10a, 10b, 10c and 10d are shown for illustration purposes in FIG. 2a. Each light ray transmitted from light source 10 enters the first prism 11 through first surface 111 (where it is refracted) and is reflected by third surface 113, before passing the second surface 112 of the first prism 11 (where it is refracted again) towards the target 3. Light ray 10a may further be indirectly incident on the third surface 113 via reflection at second surface 112. In an embodiment described below, this reflection may arise from TIR at the second surface 112. After reflection at the third surface 113, light ray 10d may further reach second surface 112 indirectly via reflection at the first surface 111. In an embodiment described below, this reflection may arise from TIR at the first surface 111. Because the rays entering the first prism 11 through first surface 111 are reflected by the third surface 113 and transmitted through the first prism 11 via the second surface 112, light leakage in the optical assembly 1 is reduced. Consequently, the flux of incident light directed towards the target 3 is increased. Due to said optical path of the treatment light, spatial and/or angular uniformity is further maintained.

In an embodiment, third surface 113 of the first prism 11 further includes a reflective coating R, so that treatment light which is incident on the third surface suffers minimal transmission losses while being reflected by the surface.

The first guiding element 12 and the first prism 11 may be disposed in contact (and hence edges 123a, 114a and edges 123b, 114b are both flush and in contact with each other), as shown in FIGS. 3a-3d, or be disposed at a separation from one another as shown in FIGS. 2a and 2b. Similarly, the second guiding element 13 and the first prism 11 may be disposed in contact (and hence edges 133a, 114b and edges 133b, 144c are both flush and in contact with each other), or be disposed at a separation from one another.

In an embodiment, side surfaces 122a and 122b of first guiding element 12, and top and bottom surfaces 132a, 132b of second guiding element 13 may further be open or closed.

With open side surfaces/faces 122a and 122b, first guiding element 12 is essentially a hollow guiding element/waveguide so that the first surface 111 is disposed in contact with air (any fluid) as medium separating the first prism 11 and the light source 10. Similarly, with open top and bottom surfaces 132a, 132b, second guiding element 13 is essentially a hollow guiding element so that the second surface 112 is disposed in contact with air (fluid) as the medium separating the first prism and the treatment aperture of the device. Treatment light may still be confined between the bound surfaces of the first and the second guiding elements 12 and 13 as indicated. The hollow guiding element allows for an optical assembly 1 with reduced weight, and thus making a device 2 incorporating the optical assembly 1 lighter. In practical implementations, such a hollow guiding element may be a pipe with reflective inner surfaces. These surfaces typically comprise a metallic layer (e.g. a layer which is deposited on a transparent substrate or a metallic foil by vacuum techniques).

Alternately, the first guiding element 12 and second guiding element 13 may be a hollow element with closed/bound side surfaces/faces 122a, 122b of first guiding element 12, and bound top and bottom surfaces 132a, 132b of second guiding element 13. In an implementation, such a guiding element may be a a closed pipe with reflective surfaces. In this case, for example, side surface 122b of first guiding element 12 and top surface 132a of second guiding element 13 may be disposed at a distance from the first surface 111 and the second surface 112 of the first prism 11, respectively.

With closed/bound side surfaces 122a, 122b of first guiding element 12, and bound top and bottom surfaces 132a, 132b of second guiding element 13, first guiding element 12 and second guiding element 13 may be a solid with appropriate refractive indices $n_1$ and $n_2$, where $n_1$ is the same as or different from $n_2$. The refractive indices $n_1$, $n_2$ of the first and the second guiding elements 12, 13, and $n_p$ of the first prism 11 may be further chosen to allow total internal reflection of light (TIR) within the first guiding elements 12, the second guiding element 13 and the first prism 11, to further minimize transmission losses (light leakage) in the optical assembly 1. Preferably, the solid guiding element may be made of transparent material with a sufficiently high refractive index to guide the angular distribution of the beam generated by the light source 10.

TIR occurs when a light ray 10a (or 10b-d) propagating in the first guiding element 12 made of a material e.g. a solid with certain refractive index (e.g. glass, $n_1$=1.5) strikes top surface 121a or bottom surface 121b which acts as boundary between the solid with higher refractive index and air having a lower refractive index (n=1) (said surfaces are disposed to be in contact with air) at an angle larger than a critical angle $\theta c$ (measured with respect to an axis/normal extending perpendicular to the top 121a or bottom 121b surface of the first guiding element 12). In this case, the light ray is entirely reflected at surfaces 121a and 121b. As a result of TIR, light transmission losses at the reflective surfaces of the first guiding element 12 are further reduced.

TIR may further occur when the light ray 10a propagating in the first prism made of a solid (e.g. glass, $n_p$=1.5) strikes surface 111, 112 or 113 which acts as boundary between the solid with higher refractive index and a medium (e.g. air, resin, solid) having a lower refractive index at an angle larger than a critical angle $\theta c$ (measured with respect to an axis/normal extending perpendicular to the respective surface of the first prism). In this case, the light ray is entirely reflected at surfaces 111, 112 and 113.

In an embodiment, the refractive index $n_1$ of the first guiding element 12 may be less than refractive index $n_p$ of the first prism 11, to satisfy the above-mentioned TIR condition.

Assuming a ray 10d which is reflected by third surface 113 of the first prism 11 is incident on the first surface 111 of the first prism 11 and satisfies TIR condition, this light ray is total internally reflected at first surface 111 and hence coupled back to the prism towards the treatment aperture. This reduces instances when a ray, after reflection by the third surface 113, leaks out of the first prism 11 into the first guiding element 12 through first surface 111. As a result of TIR at first surface 111, such light is redirected to surface 112 which either transmits the light further or reflects it to surface 113 depending on the angle of incidence of such light. Further, when guided towards the first prism 11, the light ray 10a, 10b, 10c or 10d is not total internally reflected at the surface 122b.

The arrangement therefore reduces back coupling of the light to the first guiding element in a direction towards the treatment source 10, and in turn improves the uniformity of the treatment light and increases the amount of light directed to the skin.

In another embodiment, the refractive index $n_2$ of the second guiding element 13 may be less than refractive index $n_p$ of the first prism 11.

Assuming a ray 10a which originates from first surface 111 of the first prism 11 is incident on the second surface 112 of the first prism 11 and satisfies TIR condition, this light ray (10a) is total internally reflected at second surface 112 to the third surface 113 of the first prism 11, which can then be further reflected by the third surface 113.

In an embodiment, the third surface 113 of the first prism 11 may be disposed in contact with air to allow TIR at the third surface 113 at certain angles of incidence. It may further be coated with a reflective coating R (e.g. a metallic layer) which ensures that most rays in the angular distribution of the beam generated by lamp 10 are reflected, independent of a TIR condition being satisfied at surface 113.

In an embodiment, the reflective coating may be made of a material with a lower refractive index than the first prism. Furthermore, TIR occurs when the light ray 10a (or 10b-10d) propagating in the second guiding element 13 made of a solid (e.g. glass, $n_1=1.5$) strikes side surface 131a or 131b which acts as boundary between the solid with higher refractive index and air having a lower refractive index (n=1) (said surfaces are disposed to be in contact with air) at an angle larger than a critical angle θ c (measured with respect to an axis/normal extending perpendicular to the side surface of the second guiding element 13). In this case, the light ray is entirely reflected at surfaces 131a and 131b. As a result of TIR, light transmission losses at the reflective surfaces of the second guiding element 13 are further reduced. In case of a hollow first 12 and/or second 13 guiding element with air in contact with the first surface 111 and the second surface 112 of the first solid prism 11, the refractive index restriction for TIR is implicitly achieved.

In addition to guiding treatment light which is directly emitted by light source 10 towards the target, the optical assembly 1 also guides light scattered off the target and coupled back into the device via the treatment aperture. The optical assembly 1 guides such light through the second guiding element 13 to the first prism 11 and further to the first guiding element 12 in a similar manner as the treatment light.

A (parabolic) reflector 22 may be arranged behind the light source 10 to redirect such light back through the first guiding element 12, the first prism 11 and the second guiding element 13 to the target 3. The radius of curvature of reflector 22 is sufficiently large to collect the back-scattered light and reflect it towards the first guiding element 12. The reflector 22 further functions to redirect treatment light emitted by light source 1 which is propagated in a backward direction.

As shown in FIGS. 2a and 2b, the first guiding element 12 and the first prism 11 may be separated by a predetermined gap G. In such cases, the light exit face 122b of the first guiding element 12 and the light entry face 132a of the second guiding element 13 are separated by gap G from the first surface 111 and the second surface 112, respectively, of the first prism. This is an embodiment to introduce the aforementioned refractive index variation at surfaces 111 and 112 of the first prism 11.

Assuming that TIR occurs at surfaces 121a and 121b of the first guiding element 12, and surfaces 131a and 131b of the second guiding element 13, and that rays are reflected at the third surface 113 of the first prism (either by TIR or a reflective coating), each light ray 10a, 10b, 10c, 10d is refracted at side surface 122b of the first guiding element 12, first surface 111 and second surface 112 of the first prism 11, and surfaces 132a and 132b of the second guiding element. Light rays 10a, 10b, 10c and 10d are incident on the third surface of the first prism 11 and reflected therefrom before being incident on its second surface 112 or first surface 111 and into the second guiding element 13, so that the treatment light is homogenous and light leakage is minimized. Since TIR occurs at surfaces 121a and 121b of the first guiding element 12, the third surface 113 of the first prism 11 and surfaces 131a and 131b of the second guiding element 13, light leakage is minimized at both the first and second guiding elements 12 and 13 and the first prism 11.

Leakage may occur at the gaps separating the light exit face 122b of the first guiding element 12 and the first surface 111 of the first prism 11, and the light entry face 132a of the second guiding element 13 and the second surface 112 of the first prism 11. However, this leakage can be minimized by reducing the size of gaps G, e.g. a size <100 micrometers, preferably 50-100 micrometers, more preferably 5-30 micrometers.

Although according to FIG. 2a, the gaps G between the light exit face 122b of the first guiding element 12 and the first surface 111 of the first prism 11, and the light entry face 132a of the second guiding element 13 and the second surface 112 of the first prism 11 are shown to be equal, these may also be different.

In an embodiment, the gap G further comprises a dielectric material 15. Examples of dielectrics are air (n=1), resin, oil etc. To allow TIR at surfaces 111 and 112 of the first prism 11, the dielectric material has a lower refractive index than a refractive index of the first prism 11. With air (n=1) in contact with the first surface 111 and the second surface 112 of the first solid prism 11 ($n_p$>1), the refractive index restriction for TIR is implicitly achieved. In this embodiment, the refractive indices $n_1$ and $n_2$ of the first guiding element 12 and the second guiding element 13 may be smaller, equal to or larger than the refractive index $n_p$ of the first prism 11.

Figures 4A, 4B, 4C, 4D, 4E:
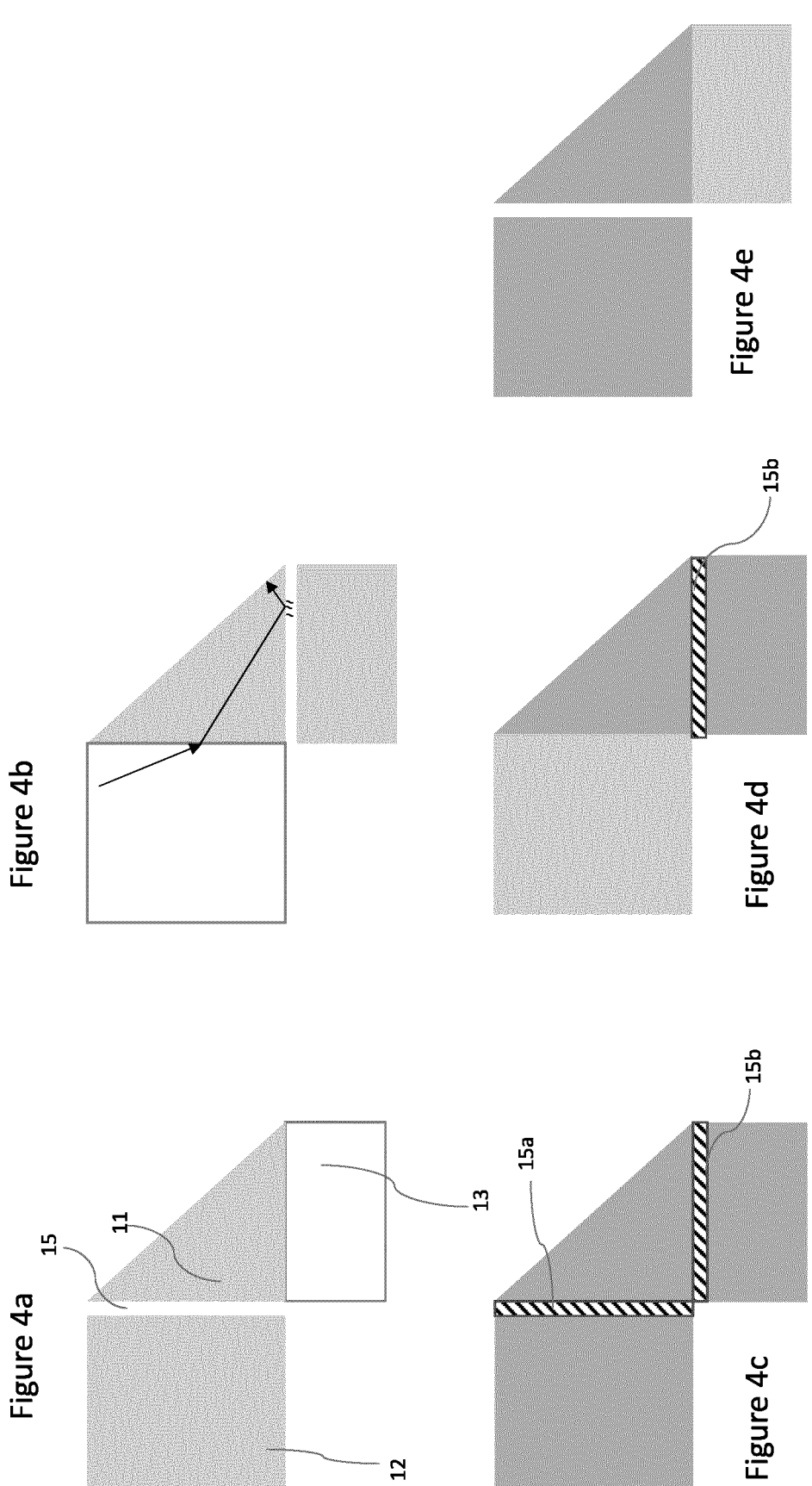
FIGS. 4a-e show optical assembly 1 according to a third exemplary embodiment of the invention.

When TIR occurs at surfaces 111 and 112 of the first prism 11 interfacing to a medium (air, resin) with lower refractive index, an evanescent wave (field) is generated adjacent to surfaces 111 and 112 of the first prism 11 in the less dense medium (e.g. in gap G). This is shown in FIG. 4b. The intensity of the evanescent wave decays exponentially from the respective surface into the gap. To prevent the evanescent wave from coupling to the first and the second guiding elements 12 and 13, it is desirable to choose the size of gap G to be sufficiently large (e.g. several micrometers) to allow decay of the evanescent wave in the gap G.

In a preferred embodiment, the gap G is chosen to be 1-100 micrometers, preferably 5-30 micrometers to reduce light leakage as well as allow decay of the evanescent wave within the gap.

Gap G may further comprise metal, glass and/or ceramic particles dispersed therein. This is illustrated in FIG. 2b. Such microparticles may be comprised of materials such as $TiO_2$, $Al_2O_3$, and AlN, and may have sizes of 1 to several tens of micrometers. Particles of such materials are thermally resistant, and mechanically strong which in turn results in a mechanically stable gap. Further, they do not absorb light in the relevant wavelength range for photoepilation. Therefore, the effect on light transmission and thus the hair or skin treatment is negligible. A minimal coverage of first surface 111 and the second surface 112 of the first prism 11 with microparticles, e.g. <0.01%, is sufficient to achieve said technical effect.

The first guiding element 12 and the second guiding element 13 may be attached to the first prism 11 by methods such as molding, by means of (polymer) resins with refractive indices similar to the guiding elements, or via contacting first and second surfaces 111 and 112 of the first prism 11 with surfaces 122b of the first guiding element 12 and 133b of the second guiding element 13 ensuring snug fit between the first guiding element 12, the first prism 11 and the second guiding element 13. The first prism 11 can be held in place by attaching the third surface 113 to a part of housing of the device 2 using suitable attachment means, e.g. with the aid of resin, or mechanically clamping a top (viewed parallel to plane of FIG. 2a or 2b) surface 115 of the first prism 11.

Although FIGS. 2a and 2b show optical assembly 1 with solid first and second guiding elements 12 and 13 each separated from the first prism 11 by gap G, as shown in FIGS. 3a-d and 4a-e, any combination of arrangements of optical assembly 1 is possible according to the invention. Hence, the above discussed embodiments in relation with FIGS. 2a and 2b can be combined without restriction in any of the disclosed embodiments FIGS. 3a-d and 4a-e.

FIG. 3a shows an exemplary embodiment of optical assembly 1 comprising a solid first prism 11 and first guiding element 12 and second guiding element 13 being hollow waveguides, so that air is in contact with the first surface 111 and the second surface 112 of the first prism 11.

FIG. 3b is an exemplary embodiment of optical assembly 1 comprising a solid first prism 11, first guiding element 12 and second guiding element 13, where the first guiding element 12 is a hollow waveguide so that air is in contact with the first surface 111 of the first prism 11 and the second guiding element 13 is a solid with surface 132a disposed in contact with the second surface 112 of the first prism 11. The refractive index $n_2$ of the second guiding element 13 may be less than the refractive index $n_p$ of the first prism 11, as shown in FIG. 3b.

FIG. 3c is an exemplary embodiment of optical assembly 1 comprising a solid first prism 11, first guiding element 12 and second guiding element 13, where the second guiding element 13 is a hollow waveguide so that air is in contact with the second surface 112 of the first prism 11 and the first guiding element 12 is a solid with surface 122b disposed in contact with the first surface 111 of the first prism 11. The refractive index $n_1$ of the first guiding element 12 may be less than the refractive index $n_p$ of the first prism 11, as shown in FIG. 3c.

FIG. 3d is an exemplary embodiment of optical assembly 1 comprising a solid first prism 11, solid first guiding element 12 and solid second guiding element 13, where the surface 122b of the first guiding element 12 is disposed in contact with the first surface 111 of the first prism 11 and the surface 132a of the second guiding element 13 is disposed in contact with the second surface 112 of the first prism 11. The refractive index $n_1$ of the first guiding element 12 and refractive index $n_2$ of the second guiding element 13 may be less than the refractive index $n_p$ of the first prism 11, as shown in FIG. 3d. FIG. 4a is an exemplary embodiment of optical assembly 1 comprising a solid first prism 11, a solid first guiding element 12 and a hollow second guiding element 13, where the first guiding element 12 is separated from the first surface 111 of the first prism 11 by gap G comprising a dielectric 15 (air, resin etc.) and the second surface 112 of the first prism 11 is disposed in contact with air. The refractive index $n_1$ of the first guiding element 12 may be less than, the same as or greater than the refractive index $n_p$ of the first prism 11. In FIG. 4a, refractive index $n_1$ is shown to be equal to refractive index $n_p$.

FIG. 4b is an exemplary embodiment of optical assembly 1 comprising a solid first prism 11, a hollow first guiding element 12 and a solid second guiding element 13, where the second guiding element 13 is separated from the second surface 112 of the first prism 11 by gap G comprising a dielectric 15 (air, resin etc.) and the first surface 111 of the first prism 11 is disposed in contact with air. The refractive index $n_2$ of the second guiding element 13 may be less than, the same as or greater than the refractive index $n_p$ of the first prism 11. In FIG. 4b, refractive index $n_2$ is shown to be equal to refractive index $n_p$.

FIG. 4c is an exemplary embodiment of optical assembly 1 comprising a solid first prism 11, a solid first guiding element 12 and a solid second guiding element 13, where the first guiding element 12 is separated from the first surface 111 of the first prism 11 by a (polymer) resin 15a and the second guiding element 13 is also separated from the second surface 112 of the first prism 11 by a (polymer) resin 15b. The refractive index $n_1$, $n_2$ of the first and second guiding element 12, 13, respectively, may be less, the same as or greater than the refractive index $n_p$ of the first prism 11. In FIG. 4c, refractive indices $n_1$ and $n_2$ are shown to be equal to refractive index $n_p$. The refractive indices $n_{r1}$, $n_{r2}$ of the polymer resins 15a, 15b may be less than the refractive index $n_p$ of the first prism 11. Further, $n_{r1}$ may be the same as or different from $n_{r2}$.

FIG. 4d is an exemplary embodiment of optical assembly 1 comprising a solid first prism 11, a solid first guiding element 12 and a solid second guiding element 13, where the first guiding element 12 is disposed in contact with the first surface 111 of the first prism 11 and the second guiding element 13 is separated from the second surface 112 of the first prism 11 by a resin 15b. The refractive index $n_1$ of the first guiding element 12 may be less than the refractive index $n_p$ of the first prism 11. The refractive indices $n_{r2}$ of the resin 15b may be less than the refractive index $n_p$ of the first prism 11. The refractive index $n_2$ of the second guiding element 13 may be less than, the same as or greater than the refractive index $n_p$ of the first prism 11. In FIG. 4d, refractive index $n_2$ is shown to be equal to refractive index $n_p$.

FIG. 4e is an exemplary embodiment of optical assembly 1 comprising a solid first prism 11, a solid first guiding element 12 and a solid second guiding element 13, where the first guiding element 12 is separated from the first surface 111 of the first prism 11 by gap G comprising air as the dielectric and the second guiding element 13 is disposed in contact with the second surface 112 of the first prism 11. The refractive index $n_2$ of the second guiding element 13 may be less than the refractive index $n_p$ of the first prism 11. The refractive index $n_1$ of the first guiding element 12 may be less than, the same as or greater than the refractive index $n_p$ of the first prism 11. In FIG. 4e, refractive index $n_1$ is shown to be equal to refractive index $n_p$. Assuming the medium between light source 10 and the first guiding element has a refractive index no, in embodiments where the first surface 111 and the second surface 112 of the first prism 11 are disposed in contact with a solid, the refractive index $n_p$ of the first prism 11 to satisfy TIR conditions in the optical assembly 1 may be calculated with respect to refractive indices $n_1$ of the first guiding element 12 and $n_2$ of the second guiding element 13 as follows.

$$n_p^2 \ge n_0^2 + n_1^2$$

$$n_p^2 \ge n_0^2 + n_2^2$$

For example, in the embodiment of FIG. 2a, assuming that the light emitted from the light source 10 travels through air to the first guiding element 12, and the first guiding element 12 and the second guiding element 13 are made of standard optical glass, $n_0$=1, $n_1$=$n_2$=1.5, so that the requirement for the prism material is $n_p \ge 1.8$. Such a refractive index can be realized in glass.

In embodiments where the first surface 111 and the second surface 112 of the first prism 11 are disposed in contact with air, the refractive indices $n_1$ of the first guiding element 12 or $n_2$ of the second guiding element 13 in the above equation are replaced by 1, i.e.

$$n_p^2 \geq n_0^2 + 1$$

The top surface 115 of the first prism 11 and the bottom surface (not shown) are disposed typically in contact with air or mechanically clamped e.g. by metal clamps, which does not influence the external refractive index and the refractive index relation between the components of the optical assembly 1.

In embodiments where the first surface 111 and the second surface 112 of the first prism 11 are disposed in contact with a resin, the refractive index $n_p$ of the first prism 11 to satisfy TIR conditions in the optical assembly 1 may be calculated with respect to refractive indices $nr_1$ of the polymer resin 15a and $nr_2$ of the polymer resin 15b is calculated as:

$$n_p^2 \geq n_0^2 + nr_1^2$$
$$n_p^2 \geq n_0^2 + nr_2^2$$

For example, in the embodiment of FIG. 4c, assuming that the light emitted from the light source 10 travels through air to the first guiding element 12, and the material of the resins 15a and 15b are chosen as 1.4 (resins with n<1.4 are equally applicable), $n_0=1$, $n_{r1}=n_{r2}=1.4$, so that the requirement for the prism material is $n_p \geq 1.72$. Such a refractive index can be realized in glass (e.g. Schott N-SF4) or optical plastic (e.g. polymers with thianthrene moieties).

The above embodiments show optical assembly 1 comprising a single first guiding element 12 between the first prism 11 and the light source 10, and a single second guiding element 13 between the first prism 11 and the treatment aperture (not shown). In an embodiment, a further light guiding element (not shown) may be disposed between the first prism 11 and the light source 10. The further light guiding element may be located adjacent to or integrated within the first guiding element 12 and may be hollow or a solid with bound reflective top surfaces flush with surface 121a of the first guiding element 12. Similarly, a further light guiding element may be disposed between the first prism 11 and the treatment aperture. There is $n_0$ restriction to the number of further guiding elements. By using further light guiding elements, the diffuse treatment light (with different propagation angles) is further collimated between the light source 10 and target 3.

FIG. 5a-e show various schematics of optical assembly 1 further comprising an optical filter 16. As mentioned, light source 10 may emit light comprising multiple wavelengths ("incoherent/white light", non-monchromatic). For example, Xenon flash lamps are capable of generating intense light within a spectral range from ultra-violet to infrared, i.e. from lower than 400 nm to as high as 1700 nm. Wavelengths below 530 nm are aborbed by hemoglobins in the blood, potentially causing discomfort and side-effects, so it is preferred that this light is filtered out. Furthermore, in case of high voltages produced on outer surfaces of light source 10, an electrical insulator may be needed in device 2 for protection against electrical hazards. To prevent unwanted radiation from being guided to the target while using device 2, and/or provide electrical insulation, a suitable filter is used in device 2.

Figure 5A:
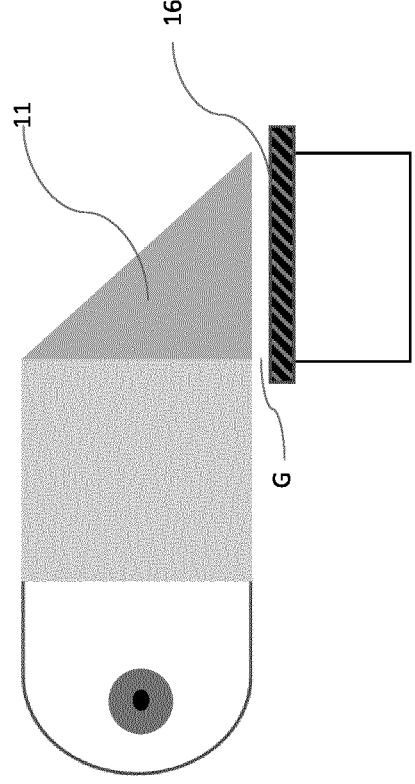
FIGS. 5a-e show optical assembly 1 according to a fourth exemplary embodiment of the invention.

In FIG. 5a, filter 16 is shown mounted above surface 132a of the second guiding element 13, proximal to the treatment aperture (not shown). Gap G, filled with either air or another dielectric with a suitable refractive index ($n_r<n_p$), between the filter 16 and the second surface 112 of the first prism 11 allows for TIR at the second surface 112 of the first prism 11. The filter 16 may have a larger cross-section than the second guiding element 13 in order to provide better electrical insulation (e.g. by increasing electrical creepage distance of the insulator). To accommodate gap G in an optical assembly 1, embodiments with filter 16 may include a larger (total) spacing between the second surface 112 of the first prism 11 and the second guiding element 13. In this embodiment, the filter 16 also functions as an insulator.

Figures 5B, 5C, 5D, 5E:
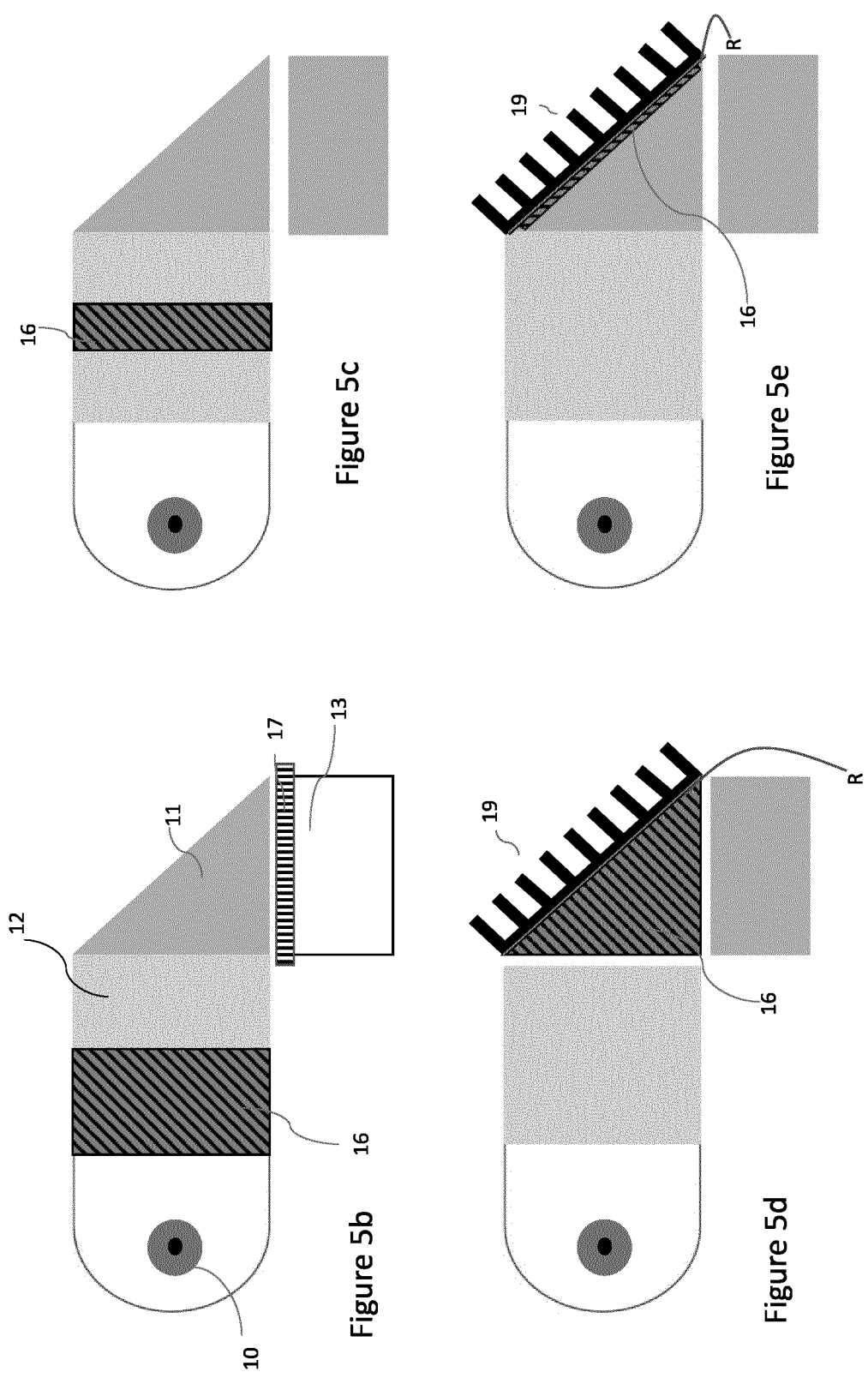

As a result of the prism-based optical assembly 1 which positions light source 10 and the treatment aperture (not shown) adjacent to target 3 in non-coaxial directions, e.g. at 90 degrees with respect to each other as shown in the above embodiments, filter 16 (e.g. optical filter) can alternately be positioned adjacent to or integrated with the first guiding element 12 (FIGS. 5b, 5c). Such optical assembly 1 offers more flexibility for incorporating additional imaging elements e.g. a camera in the line of sight of the target, e.g. along axis L' in FIG. 2a or perpendicular to L' as shown in FIG. 7, additional insulator components etc. FIG. 5b shows a transparent insulating window (e.g. made of glass) 17 sandwiched between the second surface 112 of the first prism 11 and the surface 132a of the second guiding element 13. The optical window 17 may be disposed adjacent to and/or substantially parallel to the second surface 112 of the first prism 11. Depending on the refractive index of the window, a gap G may or may not be present between the window 17 and the second surface 112 of the first prism 11. The window 17 provides electrical insulation at the exit of the the device 2 near the treatment aperture. To accommodate gap G in the optical assembly 1, embodiments with window 17 may comprise a larger (total) spacing between the second surface 112 of the first prism 11 and the second guiding element 13.

In another embodiment, the optical window 17 or the filter 16 may be disposed adjacent to and/or substantially parallel to the first surface 111 of the first prism 11.

FIG. 5d and FIG. 5e show schematics of optical assembly 1 wherein filter 16 is disposed in the first prism 11. In FIG. 5d, filter 16 is shown disposed entirely in the first prism 11 (e.g. by using doped glass as the prism material). In this case, in addition to guiding light from light source 10 to the treatment aperture, the first prism 11 also acts as the optical filter. While filter 16 blocks undesired light wavelengths, it is transparent to light wavelengths for treatment. The person skilled in the art knows how to choose a suitable filter which fulfils both purposes.

In this embodiment, the third surface 113 of the first prism 11 may be in thermal contact with a cooling member 19 (e.g. heat sink), so that the filter can be effectively cooled. This in turn protects the user of the device 2 from heat emitted by filter 16 during device operation. Furthermore, since the heat is efficiently channelled to the cooling member 19, filter 16 itself has a lower temperature (value<100° C.). A wider selection of polymer materials, which can withstand the lower temperatures, can then be used for manufacturing the filter.

The filter 16 may be disposed in contact with a reflective coating R on the third surface 113 of the first prism 11, and the cooling member then attached to the reflective coating R.

FIG. 5e shows that filter 16 may be disposed partially in the first prism 11, an outer surface of the filter 16 coexisting with the third surface 113 of the first prism 11. Light from the light source 10, when guided to the third surface 113 of the first prism 11, first passes through the optical filter 16. As a result, the light gets filtered to remove the unwanted optical wavelengths before reaching the target upon being reflected by the third surface 113. It is desirable that the refractive index of the filter 16 is similar to the refractive index of the first prism 11. This reduces light reflections at the prism-filter interface so that all incident treatment light is transmitted to the third surface 113 through the optical filter 16. Between the light source 10 and the target (skin or hair), all light passes the filter 16 twice, travelling towards the third surface 113, and travelling away from it upon being reflected. Due to this increased optical path length, the filter layer can be (less than) half the thickness of a traditional pass-through filter (e.g. <1 mm). As shown in FIG. 5e, the outer surface of filter 16 (and the third surface 113 of the first prism 11) may be disposed in contact with a cooling member 19 through a reflective coating R on the third surface 113, to further improve the cooling efficiency of the filter.

Alternately, filter 16 may be simply disposed on the third surface 113 of the first prism 11 (not shown) as a coating. In embodiments 5d or 5e, the filter 16, the reflective coating R and the cooling member 19 may be cut through to allow light from an imaging element disposed proximal to the cooling member 19 to travel through the first prism 11 to the target/skin.

Figure 6:
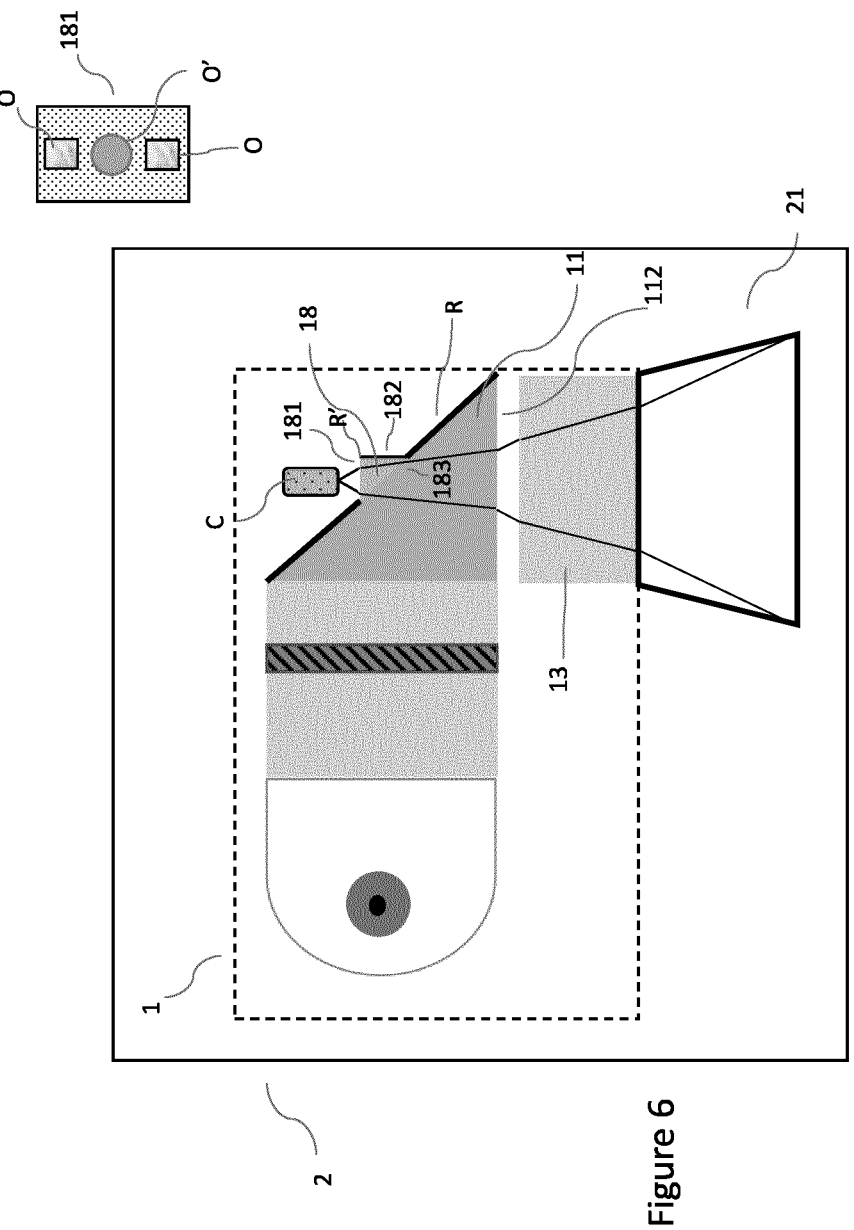
FIG. 6 shows device 2 comprising optical assembly 1 according to a fifth exemplary embodiment of the invention.

FIG. 6 shows the schematic of optical assembly 1 comprised within a light-based treatment device 2. Optical assembly 1 may be housed in a main body (shown in FIG. 10) of device 2. The device 2 may include at least one attachment 21, and the second guiding element 13 may alternately be disposed in the attachment 21 of device 2 for guiding the light output from the first prism 11 to the target 3.

The optical assembly 1 of FIG. 6 further comprises a second prism 18 (e.g. having a right triangular shape) mounted on the third surface 113 of the first prism 11. The second prism 18 comprises a first surface 181 and second surface 182 inclined with each other and a third surface 183 adjoining the first 181 and the second 182 surfaces. The refractive index $n_p$' of the second prism 18 may be similar to the refractive index $n_p$ of the first prism 11.

As mentioned, the third surface 113 of the first prism 11 (on its outer side) may further include a reflective coating R. The third surface 113 may be either fully or partially coated using this coating R.

The third surface 183 of the second prism 18 can be removably attached or fused to an uncoated portion of the third surface 113 of the first prism 11. Further, the first surface 181 of the second prism 18 may be disposed substantially parallel to the second surface 112 of the first prism 11 (perpendicular to axis L'). The second surface 182 of the second prism 18 may further include a reflective coating R' (R'= or ≠R) so that treatment light which leaks into the second prism 18 and is incident on the second surface 182 suffers minimal transmission losses at the surface. As a result of the coating, any light reaching the surface 182 of the second prism 18 is reflected into the first prism 11 for recycling. Recycling allows treatment light from light source 10 reflected off various surfaces (e.g. skin, optical components of the device) to be used again for treatment.

In an alternate embodiment in which the second guiding element 13 is shaped as a prism as shown in FIG. 7, the (e.g. third surface 183 of the) second prism 18 may be attached to an uncoated surface 131a (oblique surface/hypotenuse) of the second guiding element 13, as shown in FIG. 7. Surface 131a may comprise a full or partial reflective coating R. The first surface 181 of the second prism 18 may be disposed substantially parallel to the surface 131b of the second guiding element 13. The second surface 182 of the second prism 18 may further include a reflective coating, like mentioned above with reference to FIG. 6.

In the embodiments of FIGS. 6-8, an imaging element e.g. camera C may be further mounted on or adjacent to the first surface 181 of the second prism 18 for imaging the target (the body part). The second prism 18 is so arranged to function as a camera viewing port and entry for imaging light. In the embodiment of FIG. 6, the imaging light is incident on and transmitted through the first surface 181 and the third surface 183 of the second prism 18 disposed on the uncoated portion of the third surface 113 of the first prism, through the second surface 112 of the first prism 11 and surfaces 132a and 132b of the second guiding element 13 and the attachment 21 to the target 3. In the embodiment of FIG. 7, the imaging light is incident (not shown) on and transmitted through the first surface 181 and the third surface 183 of the second prism 18 disposed on the uncoated portion of surface 131a of the second guiding element 13, surface 131b of the second guiding element 13 to reach the target 3. Although second prism 18 is disclosed as being attached to an uncoated portion of the reflective coating of the first prism or the second guiding element, this is merely a preferred feature.

Camera C may be mounted on another element of device 2 (e.g. mounted to housing of the device 2), as long as it is suitably arranged to image the skin through the first surface 181 of the second prism 18. Hence, its position in optical assembly 1 is not limited to the embodiments of FIGS. 6-8.

The inset in FIG. 6 shows a top view of the first surface 181 of the second prism 18. The imaging light from the camera (e.g. using LEDs) may enter through light entry port(s) O to the target 3. The reflected light from the target 3 which re-enters the camera through light exit port O' may be detected by the imaging element in the camera C.

The characteristics (e.g. skin pigmentation/skin tone) of skin adjacent to a device treatment aperture via which the treatment light pulses are applied to the skin can thus be obtained. The camera C may also be used for detection of skin contact, hair count or displacement and motion of the device. For example, if no skin contact or an unsafe skin tone is detected, the device is prevented from flashing. This also offers a cost advantage by not having to incorporate dedicated contact/skin tone/motion sensors in the device.

In case of configurations FIGS. 5d and 5e, as mentioned, a cut through or a light channel (e.g. by using a suitable transmissive coating) may be further provided in the filter 16, the cooling member 19 and the coating on first prism 11, e.g. by leaving a part of the filter transparent to all visible light, a part of the surface 113 of the first prism 11 uncoated so as to allow passage of light from and to the imaging element C. The second prism 18 may be mounted on a section of the third surface 113 of the first prism 11 which is not covered by the cooling member 19. In the embodiment of FIG. 7, a further guiding element may be further be attached to surface 131b of the second guiding element 13 to guide the treatment light and imaging light to the target.

Further, the different optical path of the imaging light in this embodiment makes the presence of the mentioned light channel non-essential.

The remaining aspects of the FIGS. 6 and 7 embodiments are similar to those mentioned above and shall not be repeated here for sake of conciseness.

The embodiment of FIGS. 6-8 can be combined with any of the optical assemblies disclosed in FIGS. 2-5, or any other multi-element assembly which can be used to overcome at least one of the technical problems mentioned above.

As mentioned, the third surface 183 of the second prism 18 can be removably attached or fused to an uncoated portion of the third surface 113 of the first prism 11 or to surface 131*a* of the second guiding element 13. This is especially useful when an imaging element such as a camera C is comprised in the optical assembly 1.

Figure 8B:
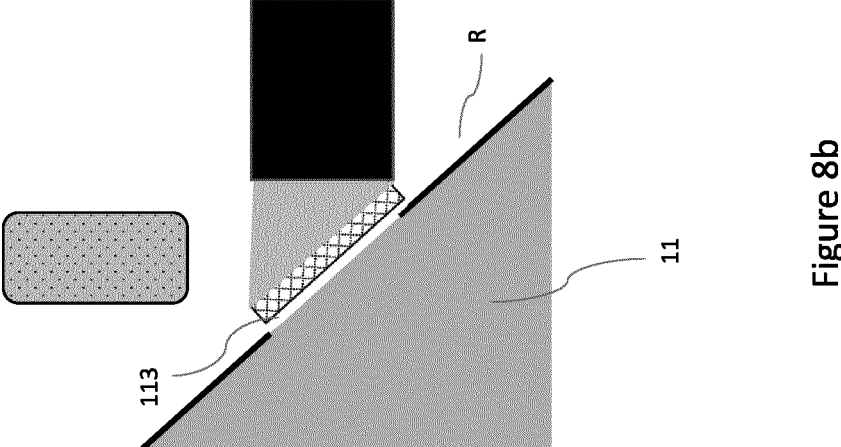
FIGS. 8a and 8b show optical assembly 1 according to an exemplary embodiment of the invention.
Figure 8A:
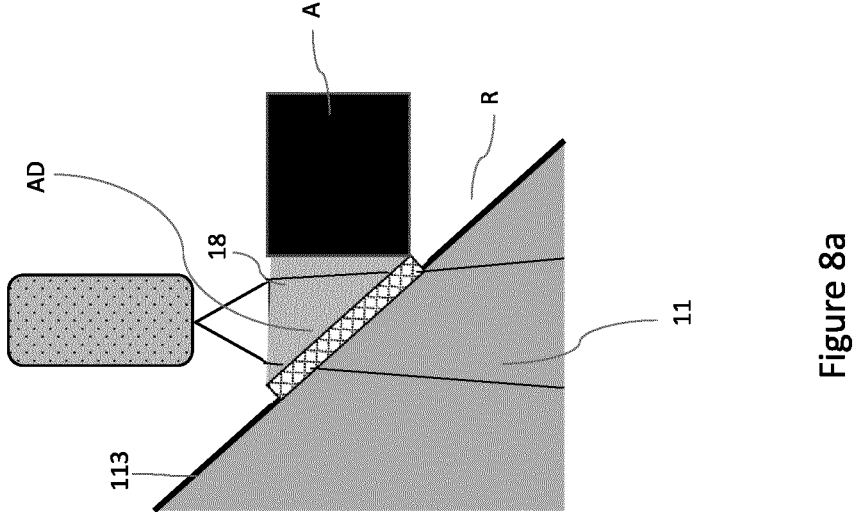

FIGS. 8*a* and 8*b* have been shown in reference to the camera configuration of FIG. 6. It can also be combined with the camera configuration described with reference to FIG. 7.

As shown in FIGS. 8*a* and 8*b*, the second surface 182 of the second prism 18 (which may be coated by reflective coating R') is connected to a movable actuator A. In a first operation mode, as shown in FIG. 8*a*, movement of actuator A causes second prism 18 to be arranged in contact with the first prism 11 (with its third surface 113). The camera C then obtains image(s) of the target 3. In this mode, the treatment light source 10 is switched off. In other words, this step is carried out before the treatment of the target using the light pulse.

The third surface 183 of the second prism 18 may further include an elastic/deformable layer AD, preferably a transparent silicone layer, which is brought in contact with the uncoated portion of the third surface 113 of the first prism 11. The deformable layer enables the prisms to have good optical contact with each other. In an embodiment, the refractive index of the deformable layer is similar to the refractive indices np' of the second prism 18 and $n_p$ of the first prism 11. In this case, in the first operation mode as shown in FIG. 8*a*, movement of actuator A causes the second prism 18 to be arranged in contact with the first prism 11 (with its third surface 113) via the deformable layer AD.

After the target characteristics is confirmed by camera C using the obtained image(s) and the target is determined safe for the light-based treatment by a controller (not shown in FIG. 8*a*/8*b*), a second operation mode is initiated. In the second operation mode, as shown in FIG. 8*b*, movement of actuator A causes second prism 18 to be disconnected from/not in contact with the first prism 11.

As a result of the second operation mode, an air gap is created between the third surface 113 of the first prism 11 and the deformable layer AD on the third surface of the second prism 18. Due to the air gap, a high (prism 11)-to-low (air) refractive index media interface is formed on the third surface 113. As a result, a large fraction of the light from the light source 10 (and light reflected from the target 3 which is coupled to device 2) is total internally reflected at the third surface 113 of the first prism 11, without damaging leakage to the second prism 18 and camera C. In this embodiment, an air gap is used as an example, however, as clear from above, any fluid can be comprised in the gap as long as its refractive index allows TIR at the third surface 113 of the first prism 11.

In this mode, optionally, the camera C may be disabled as shown in FIG. 8*b*. In combination with the retracted second prism 18, the camera C is further protected from high intensity flashes of the light source 10.

Figure 9:
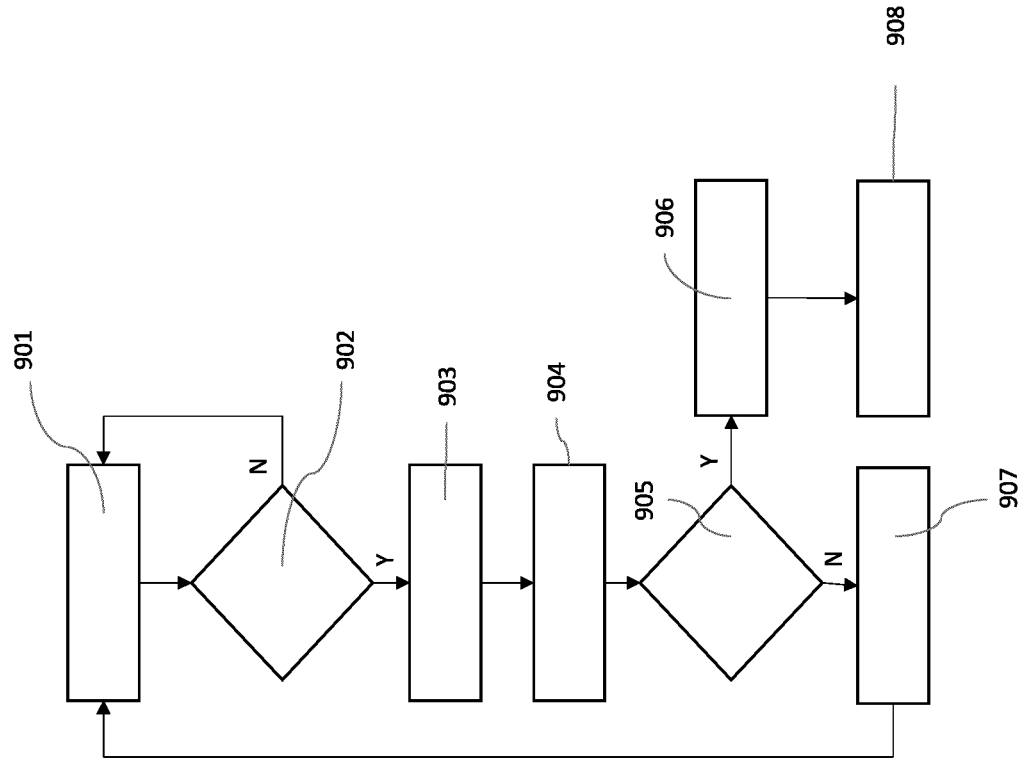
FIG. 9 shows a method according to an exemplary embodiment of the invention.

FIG. 9 shows a method for operating device 2 for cosmetic treatment according to an exemplary embodiment of the invention. Although described in reference to the structural arrangement of the imaging element as described in FIG. 6, it is also applicable to that of FIG. 7.

The method comprises providing the optical assembly 1 of any of the aforementioned embodiments. At least one image of the target 3 (either by the imaging element C or by an external imaging element/camera) is obtained to determine its suitability to treatment and thereby to determine whether to perform the treatment. If yes, the light emitted by a light source 10 of the optical assembly 1 is guided to the target for performing the treatment.

In more detail, in step 901, device 2 (main body portion or attachment) is brought in contact with target 3 (skin) for treatment. In step 902, it is determined whether contact is properly established between the device 2 and the target using a suitable skin contact sensor.

If the device controller, based on the sensor output, determines that skin contact is not established with the device, a control signal is transmitted by the controller to an interface unit connected to a display in step 902, which then informs the user to position device 2 in contact with the target 3.

If the device controller, based on the sensor output, determines that skin contact is established with the device, in step 903, a control signal is transmitted to activate actuator A of optical assembly 1. The second prism 18 is then moved towards the (uncoated) portion of the third surface 113 of the first prism 11, so that the deformable layer AD is in contact with said portion of the third surface 113.

In step 904, a control signal is transmitted to camera C of optical assembly 1. The camera C then obtains image(s) of the target 3 (skin), to determine the suitability of the skin (target 3) to the light-based treatment. Such suitability may be determined based on various skin characteristics information, e.g. skin pigmentation/tone, inferred from the image(s).

A dedicated skin contact sensor may be used for detecting contact with skin. Alternately, camera C can be used to detect skin contact. In this case, the controller transmits a control signal to activate camera C of optical assembly 1 in step 902. The controller may transmit this signal upon its activation by user e.g. via the display. The camera C obtains image(s) of the skin to detect skin contact. Steps 902 and 903 may be combined in this case. The controller may then determine, based on an image focusing quality and/or sharpness, whether contact has been established with skin. The same or a different image may then be analyzed by the controller to determine suitability of the skin to the treatment in step 904.

In step 905, the controller determines whether the skin is suitable for treatment. If suitable, in step 906, a control signal is transmitted to actuator A, to move the second prism 18 away from the uncoated portion of the third surface 113 of the first prism 11, so that the deformable layer AD is disconnected from said portion of the third surface 113. A control signal may further be transmitted to camera C so that it is disabled prior to triggering a treatment pulse from the light source 10. Once the second prism is retracted (and the camera disabled), in step 908, the control signal transmitted to the light source 10 controls the source 10 to emit the treatment light pulse.

In step 905, if the controller determines that the skin is not suitable for treatment, a control signal is transmitted to an interface unit connected to a display in step 907, which then informs the user to position device 2 on another target location. The method then resumes from step 901, till the treatment procedure is completed by the user.

Figure 10:
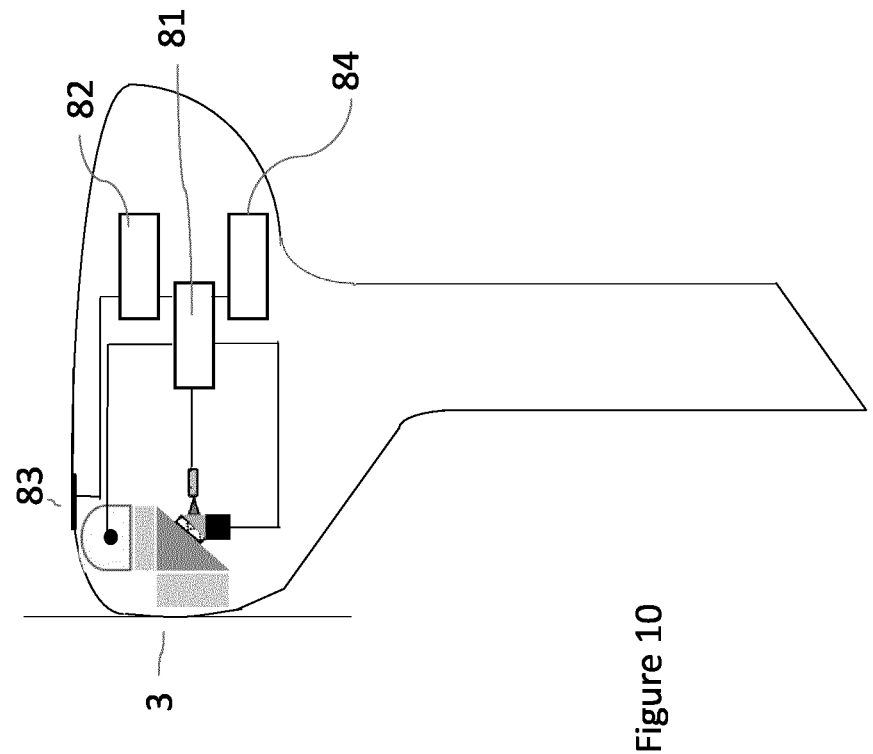
FIG. 10 shows device 2 comprising optical assembly 1 according to an exemplary embodiment of the invention.

FIG. 10 shows device 2 according to an exemplary embodiment of the present invention.

The device 2 comprises a controller 81 that generally controls the operation of the apparatus 2 and enables the device 2 to perform the method and techniques described herein.

The controller 81 is configured to transmit a control signal to the light source 10, so that the light source 10 emits light to be guided through the optical assembly 1 to target 3. It is further configured to receive one or more images from an imaging element (e.g. camera C) and processes the image(s) to determine whether device 2 is in contact with target 3 (skin). It may alternately process a contact sensor output to determine whether device 2 is in contact with the target. The controller is further configured to activate actuator A so that the imaging element can obtain image(s) or be protected from the light emitted by light source 10, and analyse the obtained image(s) to determine suitability of the skin to the light treatment. If contact is not established, or if the skin is determined to be unsuitable to treatment, the controller 81 transmits a signal to an interface unit 82 connected to a display 83, which then informs the user to re-position device 2. The controller 81 may further implement machine learning ML models such as a support vector machine, a decision tree, a random forest, an artificial neural network, a deep neural network or a convolutional neural network to perform any of the mentioned analyses or determinations.

The controller 81 can be implemented in numerous ways, with software and/or hardware, to perform the various functions described herein. The controller 81 may comprise one or more microprocessors or digital signal processors (DSPs) that may be programmed using software or computer program code to perform the required functions and/or to control components of the controller 81 to effect the required functions. The controller 81 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The controller 81 can comprise or be associated with a memory unit 84. The memory unit 84 can store data, information and/or signals (including image(s)) for use by the controller 81 in controlling the operation of the device 2 and/or in executing or performing the methods described herein. In some implementations the memory unit 84 stores computer-readable code that can be executed by the controller 81 so that the controller 81 performs one or more functions, including the methods described herein. In particular embodiments, the program code can be in the form of an application for a smart phone, tablet, laptop, computer or server. The memory unit 84 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EE-PROM), and the memory unit can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

The interface unit 82 may comprise transceivers which enable a data connection to and/or data exchange with other devices, including any one or more of servers, databases, user devices, and sensors. It can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). It may further comprise circuitry to control any suitable input component(s), including but not limited to a keyboard, keypad, one or more buttons, switches or dials, a mouse, a track pad, a touchscreen, a stylus, a camera, a microphone, etc., and the user interface can comprise any suitable output component(s), including but not limited to a display unit or display screen, one or more lights or light elements, one or more loudspeakers, a vibrating element, etc.

It will be appreciated that a practical implementation of device 2 may include additional components to those shown in FIG. 10.

The dimensions and values disclosed herein are not to be understood as being strictly limited to the exact numerical values recited. Instead, unless otherwise specified, each such dimension is intended to mean both the recited value and a functionally equivalent approximation surrounding that value. Also, unless otherwise specified, the dimensions mentioned herein are measured using common laboratory measurement techniques known to the skilled person.

While the present disclosure has been described with the above described exemplary embodiments, various changes and modifications may be suggested to one skilled in the art. It is intended that the present disclosure encompasses such changes and modifications as falling in the scope of claims.

The invention claimed is:

1. An optical assembly, for use in a skin treatment device, the optical assembly comprising:
   a light source;
   a first prism including a first surface, a second surface inclined with the first surface and a third surface adjoining the first and the second surfaces;
   a first guiding element comprising enclosed reflective faces disposed facing each other, and arranged to guide the light transmitted from the light source, through the first surface of the first prism; and
   a second guiding element comprising enclosed reflective faces disposed facing each other, and arranged to receive, through the second surface of the first prism, the light reflected from the third surface of the first prism and output the received light for illuminating the skin,
   wherein the first surface and the second surface of the first prism are separated from the first guiding element and the second guiding element, respectively, by a refractive index interface and act as total internal reflection surfaces.

2. The optical assembly of claim 1, wherein the third surface of the first prism or the reflective face of the second guiding element is coated, at least partially, with a reflective coating.

3. The optical assembly of claim 1, wherein a refractive index $n_1$ of the first guiding element and/or the refractive index $n_2$ of the second guiding element are less than a refractive index $n_p$ of the first prism.

4. The optical assembly of claim 1, wherein the reflective faces of the first light guiding element and/or the reflective faces of the second guiding element are disposed in contact with air.

5. The optical assembly of claim 1, wherein a light exit face of the first guiding element and/or a light entry face of the second guiding element are separated by a gap from the first surface of the first prism and the second surface of the first prism, respectively, wherein the gaps are the same or different.

6. The optical assembly of claim 5, wherein the gap further comprises a dielectric material which has a lower refractive index than a refractive index of the first prism.

7. The optical assembly of claim 5, wherein the gap further comprises metallic, glass or ceramic particles.

8. The optical assembly of any claim 1, further comprising a second prism having a first surface and second surface inclined with each other and a third surface adjoining the first and the second surfaces, wherein the third surface of the second prism is removably attached or fused to a portion of the third surface of the first prism or the surface of the second guiding element, and such that the first surface of the second prism is disposed substantially parallel to the second surface of the first prism or the surface of the second guiding element, and/or wherein the second surface of the second prism has a reflective coating.

9. The optical assembly of claim 8, wherein the third surface of the second prism further includes a deformable layer, and/or wherein the second surface of the second prism is connected to a movable actuator.

10. The optical assembly of claim 8, further comprising an imaging element for imaging the target through the first surface of the second prism.

11. The optical assembly of any of claim 1, further comprising an optical filter and/or an insulating window.

12. The optical assembly of claim 11, further comprising a cooling member in thermal contact with the first prism.

13. A skin treatment device comprising the optical assembly of claim 1.

14. The device of claim 13, wherein the second guiding element is disposed in a removable attachment of the device.

15. A method for performing cosmetic treatment of a target, comprising the steps of:

providing the device of claim 13;

obtaining at least one image of the target by an imaging element disposed within the device;

determining, based on at least one image of the target, whether to perform the treatment; and based on the determination, guiding light emitted by the light source of the optical assembly of device to the target for performing the treatment.

\* \* \* \* \*